US011484711B2

(12) United States Patent
Gonzalez-Martinez et al.

(10) Patent No.: US 11,484,711 B2
(45) Date of Patent: Nov. 1, 2022

(54) STEREO-THERMO-LESIONING TO TREAT A PATIENT'S NEUROLOGICAL CONDITION

(71) Applicant: THE CLEVELAND CLINIC FOUNDATION, Cleveland, OH (US)

(72) Inventors: Jorge A. Gonzalez-Martinez, Moreland Hills, OH (US); John T. Gale, Shaker Hts., OH (US); Andre G. Machado, Beachwood, OH (US); Imad Najm, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 756 days.

(21) Appl. No.: 15/659,686

(22) Filed: Jul. 26, 2017

(65) Prior Publication Data
US 2018/0028807 A1  Feb. 1, 2018

Related U.S. Application Data

(60) Provisional application No. 62/366,654, filed on Jul. 26, 2016.

(51) Int. Cl.
*A61B 18/14* (2006.01)
*A61B 18/12* (2006.01)
(Continued)

(52) U.S. Cl.
CPC ...... *A61N 1/36014* (2013.01); *A61B 18/1477* (2013.01); *A61N 1/08* (2013.01);
(Continued)

(58) Field of Classification Search
CPC ...... A61B 18/1477; A61B 2018/00446; A61B 2018/00839; A61B 2018/00791;
(Continued)

(56) References Cited

U.S. PATENT DOCUMENTS 5,769,847 A    6/1998  Panescu et al.
5,868,743 A *  2/1999  Saul ................ A61B 18/1492
                                                      606/49

(Continued)

*Primary Examiner* — Joanne M Hoffman
*Assistant Examiner* — Sean W Collins
(74) *Attorney, Agent, or Firm* — Tarolli, Sundheim, Covell & Tummino LLP

(57) ABSTRACT

This disclosure relates to using stereo-thermo-lesioning (STL) to create lesions at one or more locations in the patient's nervous system at the patient's bedside without general anesthesia. A method that uses STL to treat a patient's neurological condition includes: using a plurality of stereotactically-implanted thermo-coupled multi-contact electrodes to record conduction data within a predetermined theoretical zone of activity within the patient's neurological tissue; detecting abnormal neurological activity of a neurological condition within the conduction data and localize a portion of the predetermined theoretical zone of activity that is responsible for a primary organization of the abnormal neurological activity; creating a lesion at the portion of the predetermined theoretical zone of activity that is responsible for a primary organization of the abnormal neurological activity using at least one contact of the plurality of thermo-coupled multi-contact electrodes.

13 Claims, 7 Drawing Sheets

(51) Int. Cl.
*A61N 1/36* (2006.01)
*A61N 1/08* (2006.01)
*A61N 1/05* (2006.01)
*A61B 18/00* (2006.01)

(52) U.S. Cl.
CPC ....... *A61N 1/3606* (2013.01); *A61N 1/36082* (2013.01); *A61B 18/12* (2013.01); *A61B 2018/00446* (2013.01); *A61B 2018/00577* (2013.01); *A61B 2018/00678* (2013.01); *A61B 2018/00708* (2013.01); *A61B 2018/00791* (2013.01); *A61B 2018/00839* (2013.01); *A61B 2018/1467* (2013.01); *A61N 1/0551* (2013.01)

(58) Field of Classification Search
CPC  A61B 2018/00577; A61B 2018/00708; A61B 18/12; A61B 2018/1467; A61B 2018/00678; A61N 1/36082; A61N 1/36014; A61N 1/08; A61N 1/3606; A61N 1/0551
See application file for complete search history.

(56) References Cited

U.S. PATENT DOCUMENTS

| | | | |
|---|---|---|---|
| 6,451,011 | B2 | 9/2002 | Tu |
| 7,285,118 | B1* | 10/2007 | Lozano ............. A61B 18/1492 128/898 |
| 8,597,338 | B2 | 12/2013 | Carpentier |
| 2010/0268298 | A1* | 10/2010 | Moffitt ................. A61N 1/0534 607/45 |
| 2013/0218143 | A1* | 8/2013 | Ross ................... A61B 18/1482 606/2 |
| 2014/0094710 | A1 | 4/2014 | Sarma et al. |
| 2015/0005614 | A1* | 1/2015 | Heggeness ............... A61F 7/00 600/407 |
| 2016/0081744 | A1* | 3/2016 | Wang ..................... A61B 5/024 606/41 |

* cited by examiner

STEREO-THERMO-LESIONING TO TREAT A PATIENT'S NEUROLOGICAL CONDITION

CROSS-REFERENCE TO RELATED APPLICATIONS

This application claims the benefit of U.S. Provisional Application No. 62/366,654, entitled "SYSTEMS AND METHODS FOR CREATING ONE OR MORE LESIONS IN A PATIENT'S NERVOUS SYSTEM TO TREAT A NEUROLOGICAL CONDITION," filed 26 Jul. 2016. The entirety of this provisional application is hereby incorporated by reference for all purposes.

TECHNICAL FIELD

The present disclosure relates generally to stereo-thermo-lesioning (STL) and, more specifically, to systems and methods that use STL to treat a patient's neurological condition.

BACKGROUND

Epilepsy is among the most common disorders of the nervous system, affecting as many as 50 million people worldwide. As many as 30% of the people with epilepsy as characterized as having medically refractory epilepsy (MRE). Patients with MRE suffer from a particularly challenging form of epilepsy that is not responsive or minimally responsive to anti-epileptic drugs. A range of surgical interventions are possible for MRE, all of which rely on the precise localization of epileptogenic foci within the brain. However, even when the epileptogenic foci are localized, some patients require multiple surgical interventions, resulting in high morbidity and relatively low efficacy (approximately 50% of the patients who undergo invasive monitoring for epilepsy will fail the surgical treatment). Many patients with MRE will not be considered candidates for conventional surgical interventions due to the extent and complexity of their epileptogenic foci. In addition, many other neurological disorders, including chronic pain conditions, including neuropathic pain as well as cancer related pain, movement disorders such as Parkinson's disease, essential tremor, symptomatic tremors, other movement problems, and behavioral and psychiatric conditions continue to have poor outcomes despite management with invasive or noninvasive therapies.

SUMMARY

The present disclosure relates generally to stereo-thermo-lesioning (STL) and, more specifically, to systems and methods that use STL to treat a patient's neurological condition. Notably, STL can be used to create lesions at one or more locations in the patient's nervous system, via externalized STL leads, at the patient's bedside without general anesthesia. In some instances, the lesions can be created via externalized STL leads.

In one aspect, the present disclosure includes a method that uses STL to treat a patient's neurological condition. A plurality of stereotactically-implanted thermo-coupled multi-contact electrodes can record conduction data within a predetermined theoretical zone of activity within a patient's neurological tissue. A system comprising a processor can detect abnormal neurological activity of a neurological condition within the conduction data and localize a portion of the predetermined theoretical zone of activity that is responsible for a primary organization of the abnormal neurological activity. A lesion can be created at the portion of the predetermined theoretical zone of activity that is responsible for a primary organization of the abnormal neurological activity using at least one contact of the plurality of thermo-coupled multi-contact electrodes.

In another aspect, the present disclosure includes a system that uses STL to treat a patient's neurological or psychiatric condition. The system includes a plurality of thermo-coupled multi-contact electrodes configured to be implanted within a predetermined theoretical zone of activity within a patient's neurological tissue to record conduction data. The system also includes a computing device comprising: a non-transitory memory storing instructions; and a process configured to access the non-transitory memory and execute the instructions to at least: detect abnormal neurological activity of a neurological condition within the conduction data; localize a portion of predetermined theoretical zone of activity that is responsible for a primary organization of the abnormal neurological activity and determine at least one contact of the thermo-coupled multi-contact electrodes to apply a current to create a lesion at the portion of the predetermined theoretical zone. The system also includes a pulse generator configured to generate the current to be applied using the at least one contact of the plurality of thermo-coupled multi-contact electrodes create a lesion at the portion of the predetermined theoretical zone.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
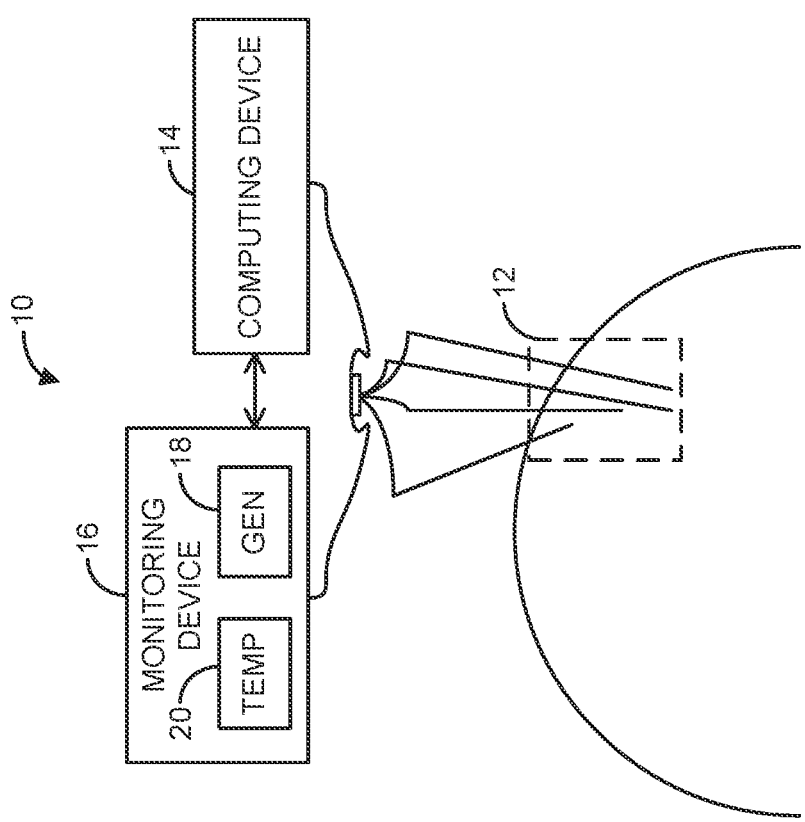
FIG. 1 is diagram of a system that uses stereo-thermo-lesioning (STL) to treat a patient's neurological condition in accordance with an aspect of the present disclosure.

In the context of the present disclosure, the singular forms "a," "an" and "the" can also include the plural forms, unless the context clearly indicates otherwise.

The terms "comprises" and/or "comprising," as used herein, can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/ steps) is not limited to the order presented in the claims or figures unless specifically indicated otherwise.

As used herein, the term "stereo-thermo-lesioning", can refer to the controlled creation of a lesion in a patient's nervous system. For example, the lesion can be created via a thermo-coupled multi-contact electrode, which was implanted into a portion of the patient's nervous system stereotactically.

As used herein, the term "thermo-coupled multi-contact electrode" can refer to a device having two or more electrode contacts coupled to one or more thermosensor devices.

As used herein, the term "electrode contact" can refer to a conductor that can establish an electrical connection with at least a portion of a patient's body. The electrical connection can be used for delivering an ablating current to the portion of the patient's body to create a lesion. However, the electrical connection can also be used for recording, stimulating applications. Electrode contacts can be constructed of different conductive materials, in different shapes, in different sizes, or the like.

As used herein, the term "thermosensor" can refer to a temperature sensor. The thermosensor can detect a rise in temperature due to creation of a lesion. In some instances, the thermosensor can be a fiber-optic thermometer.

As used herein, the term "lesion" can refer to a region of tissue that has suffered damage through injury. For example, the injury can be caused by a current that burns the tissue to create the lesion. In some instances, the lesion can be temporary, allowing for testing of whether the lesion treats the neurological condition. In other instances, the lesion can be permanent, permanently treating the neurological condition As used herein, the term "neurological condition" can refer to a disorder of at least a portion a patient's nervous system resulting from a biochemical, structural, and/or electrical abnormality, leading to abnormal neurological activity. Examples of neurological conditions can include epilepsy, a movement disorder, chronic pain, cancer pain, a psychiatric disorder, or the like.

As used herein, the term "abnormal neurological activity" can refer to anomalous electrical conduction in at least a portion of the nervous system that can be exhibited by a neurological condition.

As used herein, the term "zone of activity" can refer to a neural network that includes nodes that are responsible for the generation and/or propagation of the abnormal brain activity. In some instances, the zone of activity can refer to an epileptogenic zone (EZ) that includes nodes within a specific neural network responsible for the generation of the abnormal brain activity. For example, the EZ may include the focus or foci of a seizure.

As used herein, the terms "target area" and "theoretical zone of activity" can refer to an area corresponding to an initial estimate of a suspected zone of activity of a neurological condition based on pre-operative non-invasive data. A thermo-coupled multi-contact electrode can be implanted to a specific location in the target area to determine the actual zone of activity.

As used herein, the term "conduction data" can refer to data included in signals recorded by one or more contacts of the thermo-coupled multi-contact electrode. In some instances, the conduction data can be used to construct an electroencephalogram (EEG) showing conduction in at least a portion of the nervous system.

As used herein, the term "nervous system" can refer to at least a portion of the brain, the spinal cord, and/or the peripheral nervous system.

As used herein, the term "stereotactic" can refer to a technique for locating one or more points inside a target area in a patient's brain using an external, three-dimensional frame of reference based on a three-dimensional coordinate system. For example, a plurality of thermo-coupled contact-electrodes can be implanted within a plurality of specific locations in a target area using a stereotactic implantation device.

As used herein, the term "medical professional" can refer to can refer to any person involved in medical care of a patient including, but not limited to, physicians, medical students, nurse practitioners, nurses, and technicians.

As used herein, the term "patient" can refer to any warm-blooded organism including, but not limited to, a human being, a pig, a rat, a mouse, a dog, a cat, a goat, a sheep, a horse, a monkey, an ape, a rabbit, a cow, etc. The terms "patient" and "subject" can be used interchangeably herein.

II. Overview

The present disclosure relates generally to stereo-thermo-lesioning (STL) and, more specifically, to systems and methods that use STL to treat a patient's neurological condition. The neurological condition that can be treated by STL can include epilepsy, a movement disorder, chronic pain, cancer pain, a psychiatric disorder, or the like. Using STL, one or more lesions can be created in a patient's neural tissue at the patient's bedside without the need for general anesthesia. The lesions can be temporary, allowing for testing of whether the lesion treats the neurological condition. However, alternatively, the lesions can be permanent, permanently treating the neurological condition.

STL can be accomplished using special thermo-coupled multi-contact electrodes. A plurality of such thermo-coupled multi-contact electrodes can be implanted into the patient's nervous system in a predetermined theoretical zone of activity. Conduction data can be recorded that indicates abnormal neural activity of the neurological condition. Based on the conduction data, a portion of the zone of activity can be localized that is responsible for a primary organization of the abnormal neural activity. Then, using at least one contact of the plurality of thermo-coupled multi-contact electrodes, the one or more lesions can be created within the portion of the zone of activity that is responsible for a primary organization of the abnormal neural activity.

III. Systems

One aspect of the present disclosure can include a system 10 uses stereo-thermo-lesioning (STL) to treat a patient's neurological condition. The neurological condition can arise anywhere in the patient's central or peripheral nervous system and can be treated with STL. However, a neurological condition of the brain will be described herein as an example. The neurological condition can be, for example, epilepsy, a psychiatric disorder, a movement disorder, chronic pain, cancer pain, or the like.

Using STL, a temporary/reversible or permanent lesion can be created in the patient's brain in a minimally-invasive manner. For example, the lesion can be created by a burst of current to a specific area of the patient's brain for a short time. Properties like a temperature rise and/or a decrease in abnormal conduction can be recorded by the STL lead and system 10 to control how the lesion is created. Because the STL leads are implanted in the brain for externalized bedside monitoring, the lesion can be created at the patient's bedside without the need for general anesthesia or an operating room. System 10 can form a lesion with far less expense (e.g., monetary, mortality, and/or morbidity) than traditional treatment for neurological conditions.

The system 10 can include a plurality of thermo-coupled multi-contact electrodes 12, a computing device 14, and a monitoring device 16 that can operate together to perform STL on the patient's brain. In some instances, STL can include the creation of a temporary and/or reversible lesion at a location in the patient's brain. In other instances, the lesion can be a permanent lesion that treats the neurological condition. In some instances, the computing device 14 can be part of the monitoring device 16. In other instances, the computing device 14 can be separate from the monitoring device 16. The computing device 14 and/or the monitoring device 16 can include a processor that can implement instructions stored in a non-transitory memory. In some instances, the non-transitory memory (e.g., not a transitory signal) can also be included with the computing device 14 and/or the monitoring device 16.

The plurality of thermo-coupled multi-contact electrodes 12 can be configured to be implanted within a predetermined theoretical zone of activity within a patient's neurological tissue. The predetermined theoretical zone of activity can be determined based on previously recorded data. The previously recorded data can be recorded via a non-invasive or minimally-invasive means, like an imaging means, a surface electroencephalogram (EEG) means, or the like. The plurality of thermo-coupled multi-contact electrodes 12 can be implanted at a plurality of locations within the predetermined theoretical zone of activity.

Each of the thermo-coupled multi-contact electrodes 12 can include a plurality of electrical contacts that can be configured to record electrical conduction data from different areas within the predetermined target area of the brain. The conduction data recorded by each contact can be related to the portion of the brain surrounding the respective contact. Each electrical contact can also be configured to deliver an ablative current to an area of the brain. In one example, the plurality of thermo-couple multi-contact electrodes 12 can provide between 100-200 (or more) electrical contacts. The electrical contacts can be of different sizes, shapes, and/or materials.

Figure 2:
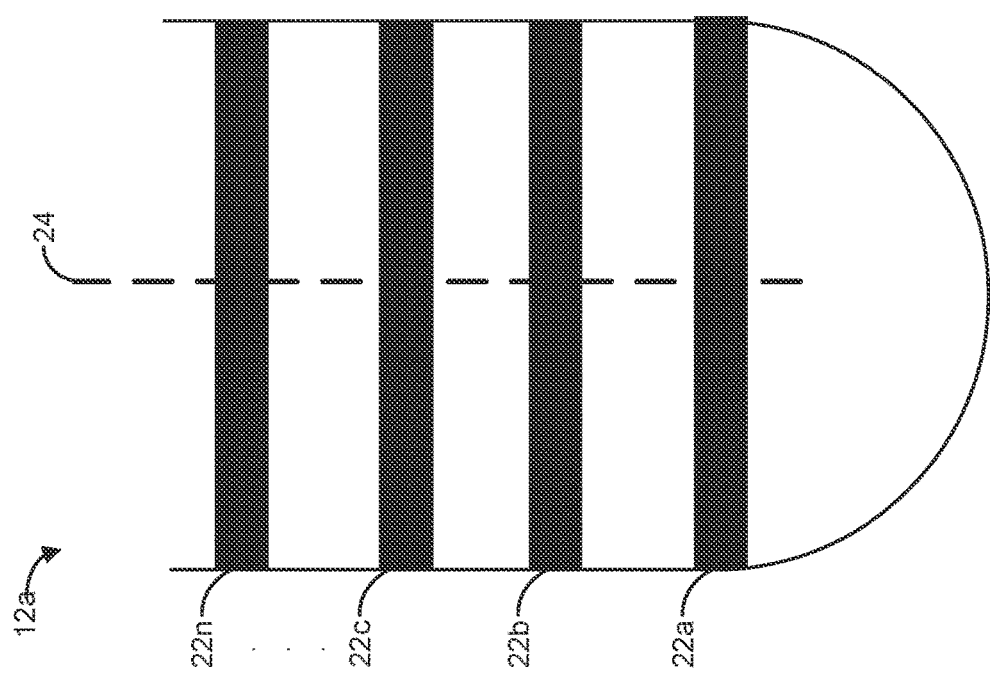
FIG. 2 is a diagram of one of the thermo-coupled multi-contact electrodes in FIG. 1.

An example of one thermo-coupled multi-contact electrode 12*a* is shown in FIG. 2, with a plurality of electrical contacts 22*a*-22*n* (where a=1 and n=a value greater than or equal to 2, limited by the size and/or shape of the electrode) and a thermosensor 24 (e.g., a fiber-optic thermometer) coupled to at least one of the electrical contacts 22*a*-22*n*. Each multi-contact electrode can have 2 or more electrical contacts. However, in other examples, each multi-contact electrode can have 4 or more electrical contacts. In still other examples, each multi-contact electrode can have 10 or more electrical contacts. The thermosensor 24 can monitor a temperature rise while a lesion is created by at least one of the electrical contacts 22*a*-22*n*. Based on the detected temperature rise, the current can be stopped when the temperature rises to a predetermined threshold value indicating the lesion is fully formed.

The plurality of thermo-coupled multi-contact electrodes 12 can be implanted into the various positions in the target area. In some instances, the implantation of the individual thermo-coupled multi-contact electrodes 12 can be at pre-defined locations and/or at predefined depths. In other instances, the implantation of the thermo-coupled multi-contact electrodes 12 can be at a variety of locations and/or depths in the target area of the patient's brain. In still other instances, the implantation of the individual thermo-coupled multi-contact electrodes 12 can include implantation of one or more of the thermo-coupled multi-contact electrodes 12 outside the target area. The implantations can be at various depths within the brain, requiring different implantation trajectories. In some instances, the plurality of thermo-coupled multi-contact electrodes 12 can be implanted by a stereotactic procedure. Although four thermo-coupled multi-contact electrodes 12 are illustrated, it will be understood that any number of thermo-coupled multi-contact electrodes 12 greater than two can be used. In one example, 10-15 thermo-coupled multi-contact electrodes 12 of different sizes and shapes can be implanted into the patient's brain.

Figure 3:
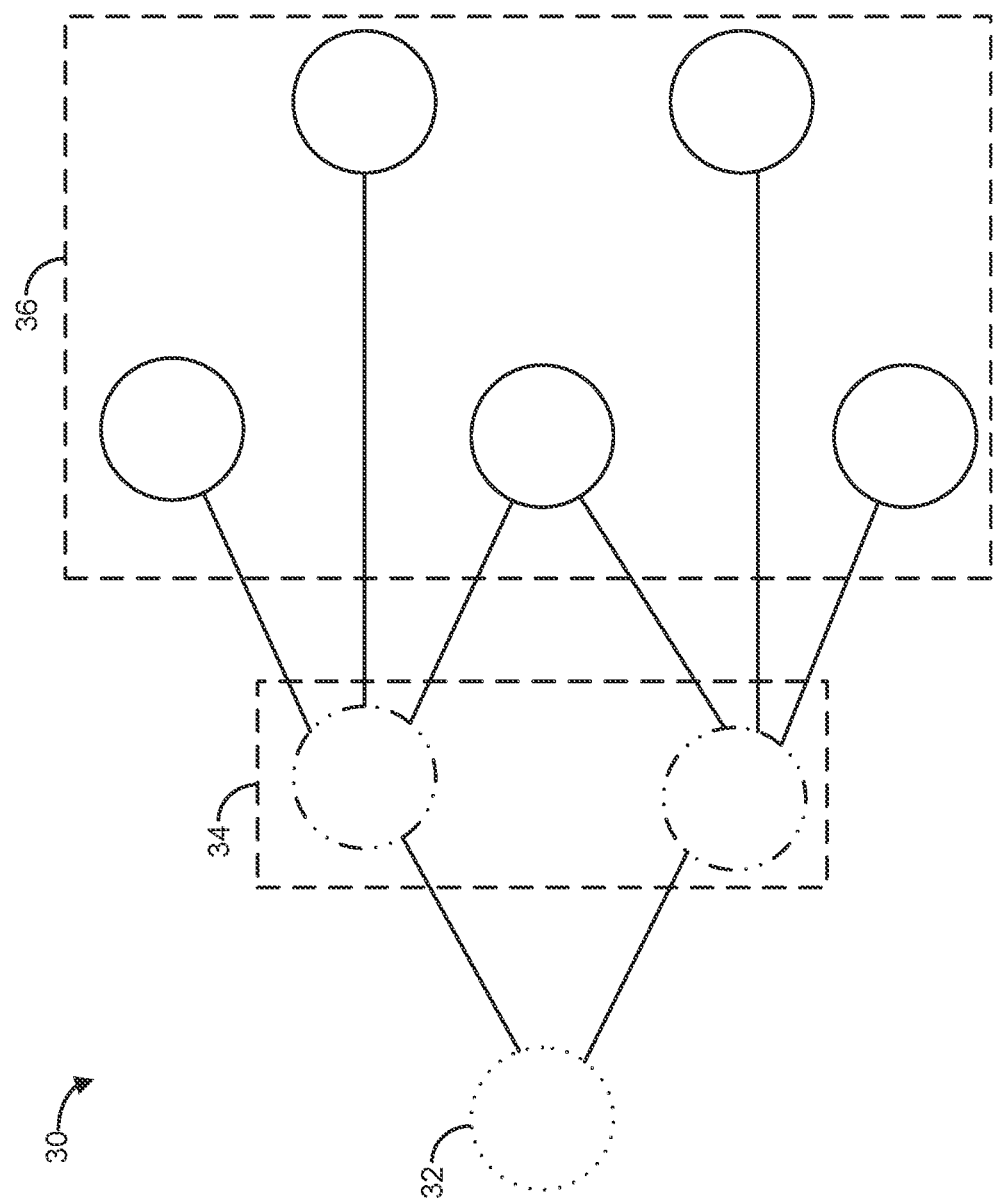
FIGS. 3-5 illustrate example neuronal networks and the associated nodes to be ablated by the system of FIG. 1.
Figure 4:
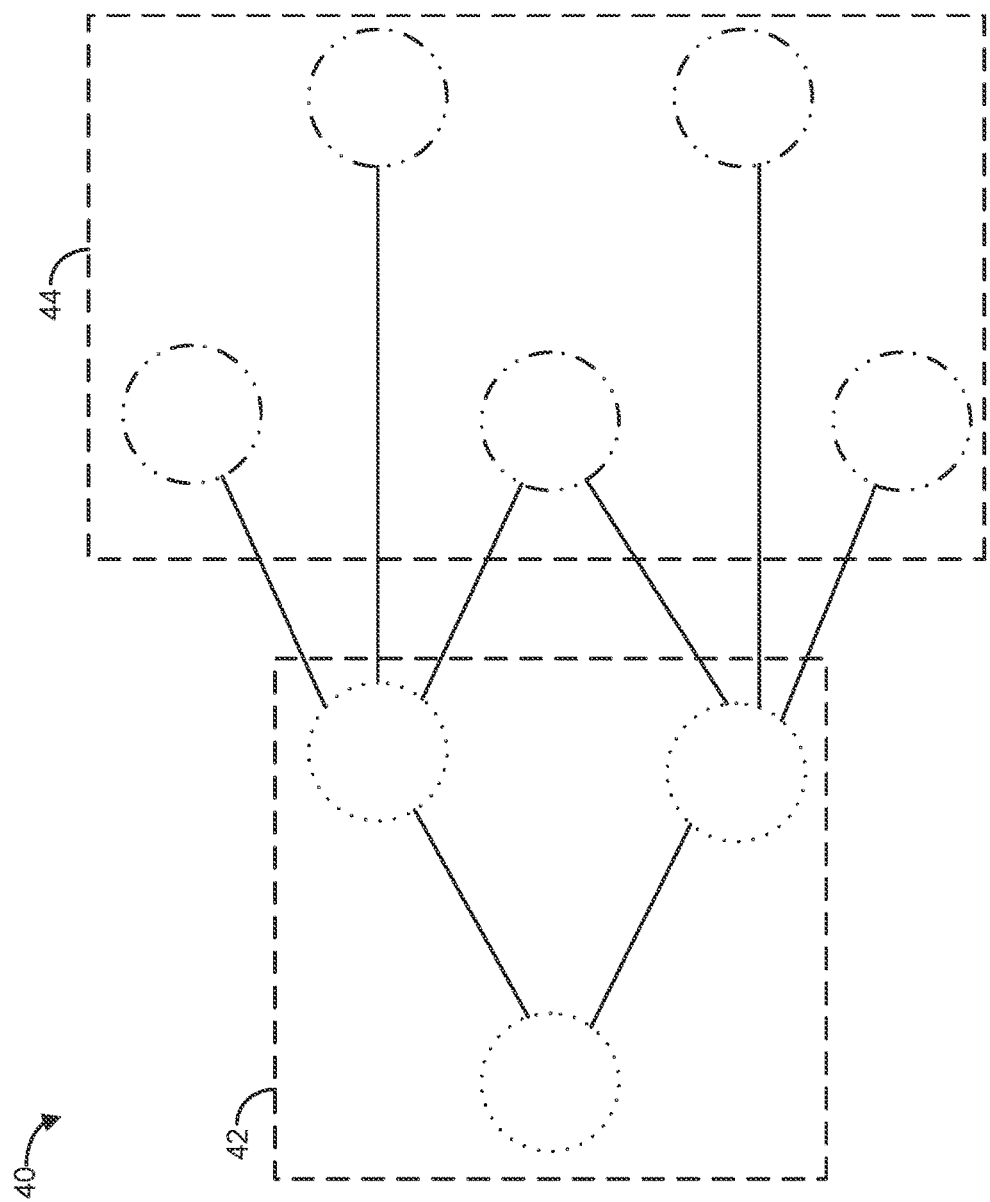
Figure 5:
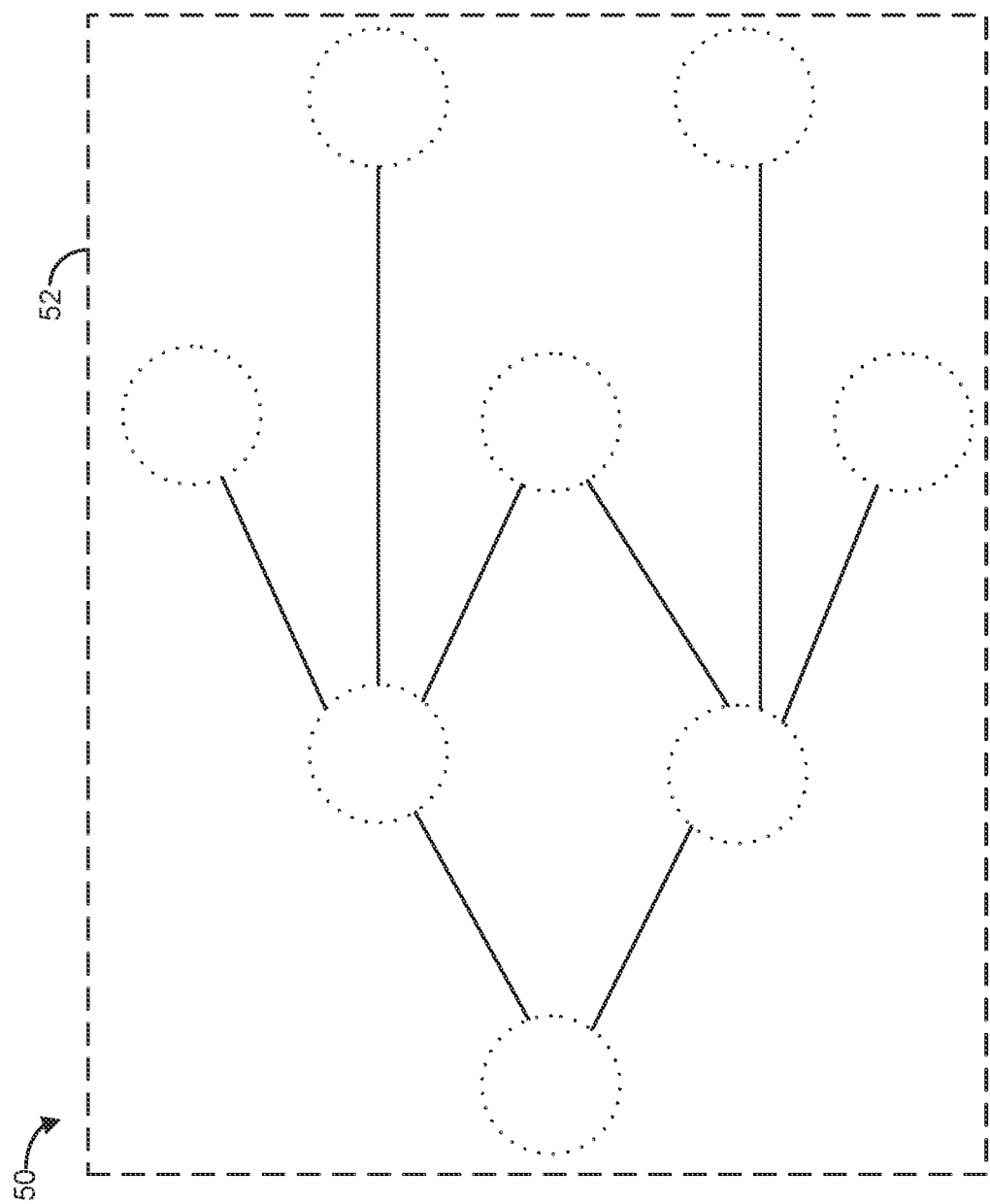

The conduction data, recorded by each contact, can be sent to the computing device 14 for further analysis. For example, the conduction data can be used to provide clinical and computational analyses (that can include frequency and centrality analyses) to determine a portion of a predetermined theoretical zone of activity (e.g., various nodes illustrating the propagation of the abnormal conduction are shown in FIGS. 3-5) that is responsible for a primary organization of an abnormal brain activity contributing to the neurological condition.

Based on the conduction data, a portion of the predetermined theoretical zone of activity that is responsible for a primary organization of the abnormal brain activity can be localized by the computing device 14. FIGS. 3-5 show example zones of activity that can be identified by the computing device 14. In FIG. 3, the conduction map 30 indicates that the zone of activity 32 includes a single node, the zone that propagates the abnormal brain activity 34 includes two nodes, and the unaffected zone 36 includes five nodes. Accordingly, the area of ablation can include the one node of the zone of activity 32. In FIG. 4, the conduction map 40 indicates that the zone of activity 42 includes three nodes, and the zone that propagates the abnormal brain activity 44 includes five nodes. Therefore, the area of ablation can include the three nodes of the zone of activity 42. In FIG. 5, the conduction map 50 indicates that the zone of activity 52 includes eight nodes, and the area of ablation can include all eight nodes in the zone of activity 42.

The computing device 14 and/or the monitoring device 16 can determine at least one of the contacts on at least one of the plurality of thermo-coupled multi-contact electrodes 12 to deliver the ablation to cause the lesion at the determined particular location in the patient's brain. The ablative current can be generated by a pulse generator.

In some instances, the determined contacts can deliver an ablative current to the particular location in the patient's brain that can cause the lesion. The lesion can be reversible/temporary and/or permanent. The monitoring device 16 can control the generation of the ablation current by the pulse generator (gen 18) and can monitor the temperature (temp 20) from the thermosensor associated with the ablation. For example, the monitoring device 16 can control the generation of the ablation by setting the ablative current. Also for example, the monitoring device 16 can monitor a rise in temperature (temp 20) associated with the ablation based on a recording by a thermosensor of at least one of the plurality of thermo-coupled multi-contact electrodes 12. Additionally, the contacts of the plurality of thermo-coupled multi-contact electrodes 12 can record the conduction data during the ablation. The computing device 14 can determine when the abnormal brain activity is reduced or stopped because of the lesion. In some instances, a second lesion can be placed by the same or different one of the contacts in a same or different area so that the abnormal brain activity is reduced or eliminated. When the lesion is reversible/temporary, it can be determined whether the lesion treats the abnormal brain condition. When the lesion is determined as treating the neurological condition, the reversible/temporary lesion can be replaced by a permanent lesion. When the reversible/temporary lesion is determined not to effectively treat the neurological condition, another contact can be created at another location in the target area. The other location can be based on another node in the neurological network contributing to the abnormal conduction (shown in FIGS. 3-5).

The monitoring of activity from the brain can occur with the individual at rest, or under general anesthesia, in order to capture or record spontaneous events such as seizure, abnormal movement, psychiatric episode, pain or other neurological symptoms. Alternatively, the activity of the brain may also be recorded along with an event that produces or alters baseline brain activity. For example, the patient may be presented with a sensory or painful stimulus in order to help characterize the brain activity associated with pain or pain anticipation. In another example, the patient may be presented with visual stimuli with a given contextual meaning or valence while the system is recording and processing brain activity. In another example the patient may be given auditory or any other type of sensory stimulation in order to study event related phenomena.

IV. Methods

Figure 6:
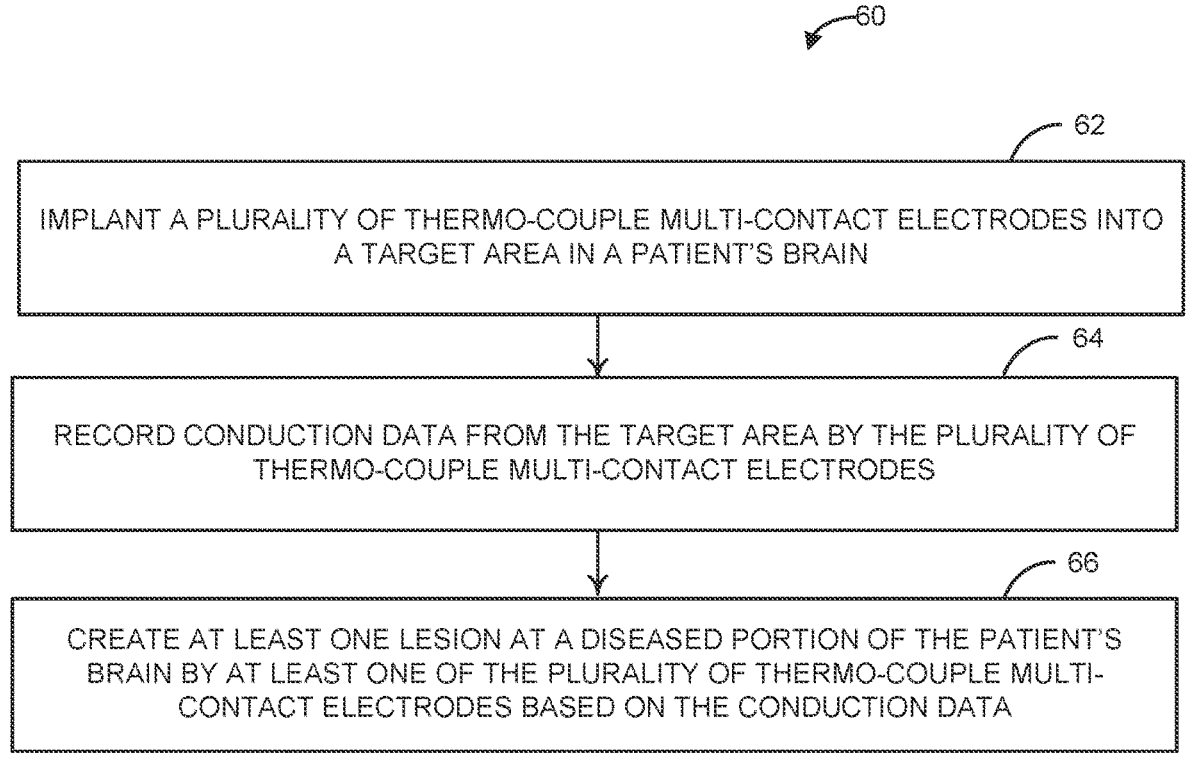
FIGS. 6 and 7 are process flow diagrams illustrating methods for creating a lesion in the patient's brain to treat a neurological condition with STL in accordance with another aspect of the present disclosure.
Figure 7:
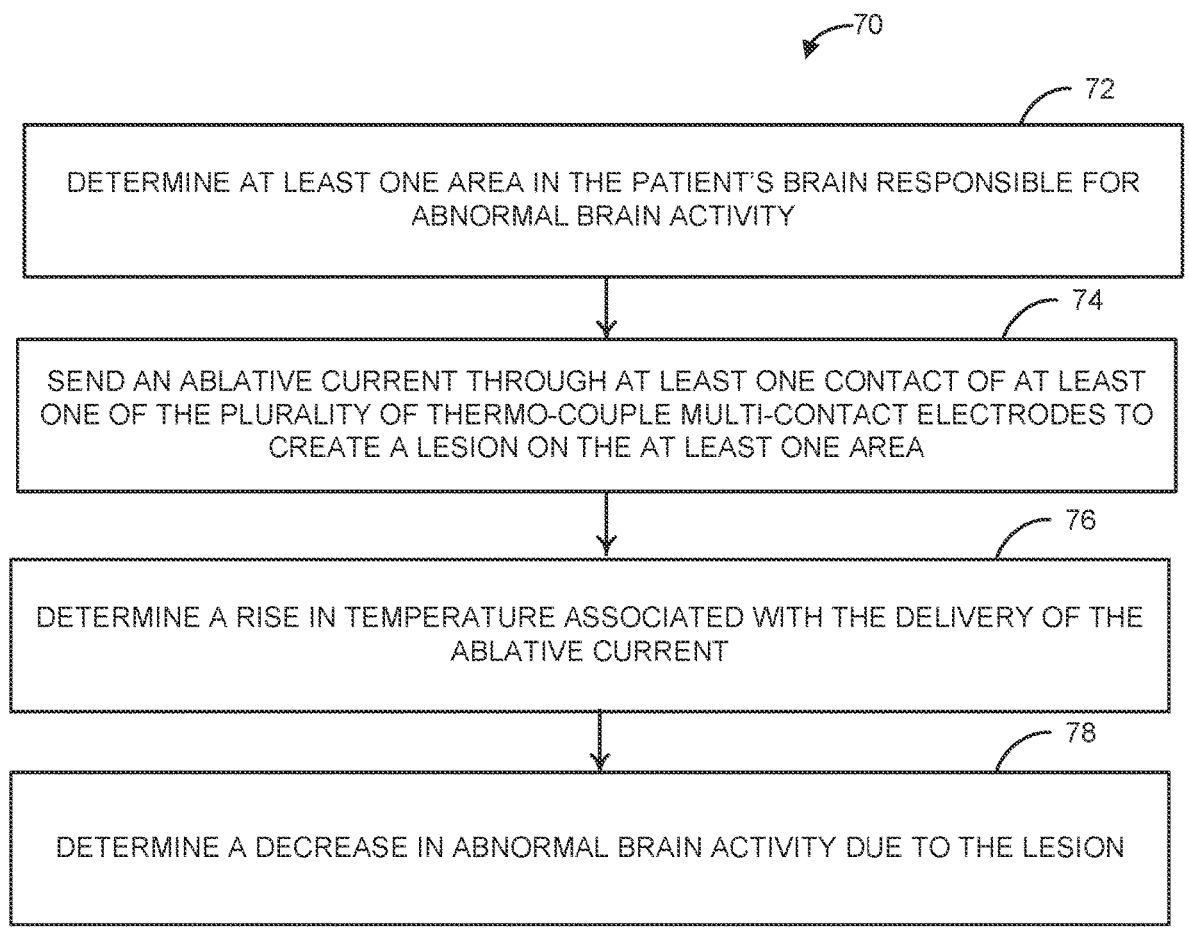

Another aspect of the present disclosure can include methods 60 and 70 for creating a lesion in the patient's brain to treat a neurological condition with stereo-thermo-lesioning (STL), as shown in FIGS. 6-7. The lesion can be used to treat a neurological condition, such as epilepsy, a psychiatric disorder, or the like. As an example, the methods 60 and 70 can be accomplished using the system 10 as shown in FIG. 1.

The methods 60 and 70 are illustrated as process flow diagrams with flowchart illustrations. For purposes of simplicity, the methods 60 and 70 are shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the methods 60 and 70.

FIG. 6 illustrates a method 60 for creating a lesion in a patient's brain to treat a neurological condition. In some instances, the method 60 can be a minimally-invasive STL method that can be performed at the patient's bedside, with no need for general anesthesia and expensive operating rooms.

At 62, a plurality of thermo-couple multi-contact electrodes (e.g., as illustrated in FIG. 2) can be implanted at specific locations in a target area in the patient's brain. The target area can correspond to a predetermined theoretical zone of activity within the patient's brain. In some instances, the implantation of the plurality of thermo-couple multi-contact electrodes can utilize a stereotactic technique. The specific locations and depth of implantation of the plurality of thermo-couple multi-contact electrodes in the target area can be determined based on previous non-invasively collected data (e.g., imaging data, surface EEG data, etc.) and/or previous invasively-collected data (as in stereo-electroencephalography or guided by subdural grids and strips). In some instances, 10-15 (or more) thermo-couple multi-contact electrodes of different sizes and/or shapes can be implanted to specific locations and at varying depths within a target area of the patient's brain.

At 64, each of the plurality of thermo-couple multi-contact electrodes can record conduction data from the target area. Each of the plurality of thermo-couple multi-contact electrodes can record conduction data from its respective specific location in the target area. The plurality of thermo-couple multi-contact electrodes can provide between 100-200 (or more) recording contacts of different sizes, shapes, and/or materials. The conduction data recorded by the plurality of thermo-couple multi-contact electrodes can be used to provide clinical and computational analyses (that can include frequency and centrality analyses) to determine a portion of the target area (e.g., shown in FIGS. 3-5) that is responsible for a primary organization of an abnormal brain activity contributing to the neurological condition.

The plurality of thermo-couple multi-contact electrodes can record conduction data for a time period. The conduction data can include the abnormal brain activity. In some instances, the abnormal brain activity can be visualized as a conduction map, which can provide a colored visualization of the abnormal conduction.

At 66, a lesion can be created at a diseased portion of the patient's brain by at least one contact of at least one of the plurality of thermo-couple multi-contact electrodes based on the conduction data. The lesion can be small, but strategically located in the zone of activity determined based on the conduction data. Multiple lesions can be created (and the process repeated multiple time) until the abnormal brain activity is completely extinguished. The thermo-couple multi-contact electrodes can have a coupled thermosensor (e.g., a fiber-optic thermometer) to detect a rise in temperature associated with the lesion. The rise in temperature can be correlated to a decrease in the abnormal brain activity shown in the conduction data recorded at the same time.

For example, the lesion can be formed by passing a small amount of ablative current through a pre-defined contact of the at least one of the plurality of thermo-couple multi-contact electrodes. A method 70 is shown in FIG. 7, in which an ablative current is used to generate the lesion. At 72, at least one area in the patient's brain responsible for abnormal brain activity can be determined. This determination can be based on conduction data recorded by a plurality of thermo-couple multi-contact electrodes that are at pre-determined locations in the patient's brain. For example, the conduction data recorded by the plurality of thermo-couple multi-contact electrodes can be used to provide clinical and computational analyses (that can include frequency and centrality analyses) to determine a zone of activity (e.g., shown in FIGS. 3-5) that is responsible for a primary organization of an abnormal brain activity contributing to the neurological condition. In addition, in order to test the localization hypothesis, sublethal, non-permanent lesions can be created in several locations and sizes. Once it is confirmed that a sublethal lesion can extinguish the abnormal activity (e.g., epileptiform activity/pain/abnormal movement disorder, etc.) a permanent lesion is created.

A location for lesion formation can be determined based on an analysis of the conduction data. The analysis can be based on the frequency of the abnormal brain activity and/or a centrality of the abnormal brain activity. At 74, an ablative current can be sent through at least one contact of at least one of the plurality of thermo-coupled multi-contact electrodes to create a lesion on the at least one area. The lesion can be reversible/temporary and/or permanent. At 76, as the lesion is created, a rise in temperature can be determined associated with the delivery of the ablative current. For example, a thermosensor (e.g., a fiber-optic thermometer) coupled to the multi-contact electrodes of at least one of the plurality of thermo-coupled multi-contact electrodes can monitor the rise in temperature due to creating the lesion. Simultaneously, at 78, the multi-contact electrode can record a decrease (e.g., indicating the progressive vanishing) of the abnormal brain activity corresponding to the neurological condition due to the lesion.

When the lesion is reversible/temporary, it can be determined whether the lesion treats the abnormal brain condition. When the lesion is determined as treating the neurological condition, the reversible/temporary lesion can be replaced by a permanent lesion. When the reversible/temporary lesion is determined not to effectively treat the neurological condition, another contact can be created at another location in the target area. The other location can be based on another node in the neurological network contributing to the abnormal conduction (shown in FIGS. 3-5).

From the above description, those skilled in the art will perceive improvements, changes and modifications. Such improvements, changes and modifications are within the skill of one in the art and are intended to be covered by the appended claims.

What is claimed is:

1. A method comprising:
   determining, by a system comprising a processor, a predetermined theoretical zone of activity based on previously recorded data, wherein a plurality of thermo-coupled-multi-contact electrodes, each comprising a plurality of contacts configured for recording and ablation and at least one temperature sensor, are implanted within the predetermined theoretical zone of activity within a patient's brain;
   receiving, by the system, conduction data within the predetermined theoretical zone of activity recorded by the plurality of the contacts of the plurality of thermo-coupled-multi-contact electrodes;
   defining, by the system, a neurological network within a portion of the predetermined theoretical zone of activity responsible for generation of an abnormal neurological activity based on the conduction data;
   detecting, by the system, an occurrence of the abnormal neurological activity of a neurological condition within the neurological network;
   localizing, by the system, a portion of the predetermined theoretical zone of activity that is responsible for a primary organization of occurrence of the abnormal neurological activity, wherein the portion of the predetermined theoretical zone of activity comprises at least one node of the neurological network;
   selecting, by the system, at least two contacts of the plurality of implanted thermo-coupled multi-contact electrodes that are at or near the at least one node of the neurological network to create a temporary lesion within the portion of the predetermined theoretical zone of activity comprising the at least one node of the neurological network, wherein the temporary lesion is created by delivering a controlled ablative current through the at least two contacts of the plurality of implanted thermo-coupled multi-contact electrodes that are at or near the at least one node of the neurological network and monitoring an associated temperature;
   receiving, by the system, conduction data within the predetermined theoretical zone of activity recorded by the plurality of the contacts of the plurality of thermo-coupled-multi-contact electrodes during the delivery of the controlled ablative current; and
   determining, by the system, whether the temporary lesion stops the abnormal neurological activity and treats the neurological condition, wherein:
      when the temporary lesion is determined to treat the neurological condition based on the conduction data recorded during the delivery of the controlled ablative current, a permanent lesion is created at the at least one node of the neural network, and
      when the temporary lesion is determined not to treat the neurological condition based on the conduction data recorded during the delivery of the controlled ablative current ablation, another contact of the plurality of thermo-coupled multi-contact electrodes is selected to create another temporary lesion at another at least one node of the neural network.

2. The method of claim 1, wherein the localizing further comprises analyzing a frequency of the abnormal neurological activity and/or a centrality of the abnormal neurological activity.

3. The method of claim 1, wherein the defining the neurological network further comprises creating a map based on conduction data recorded by the plurality of thermo-coupled multi-contact electrodes before the delivery of the controlled ablative current.

4. The method of claim 1, further comprising:
   monitoring, using the temperature sensor, a temperature rise while the temporary lesion is created; and
   stopping, by the system, a current being applied by the at least two contacts of the plurality of thermo-coupled multi-contact electrodes when the temperature rise rises to a threshold value indicating the temporary lesion is fully formed.

5. A system comprising:
   a plurality of thermo-coupled multi-contact electrodes, each comprising a plurality of contacts configured for recording and ablation and at least one temperature sensor, configured to be implanted within a predetermined theoretical zone of activity within a patient's brain;
   a computing device comprising:
      a non-transitory memory storing instructions; and
      a processor configured to access the non-transitory memory and execute the instructions to at least:
         receive conduction data within the predetermined theoretical zone of activity recorded by the plurality of contacts of the plurality of thermo-coupled-multi-contact electrodes;
         define a neurological network within a portion of the predetermined theoretical zone of activity responsible for generation of an abnormal neurological activity within the patient's brain based on the conduction data;
         detect the abnormal neurological activity of a neurological condition within the neurological network;
         localize a portion of the predetermined theoretical zone of activity that is responsible for a primary organization of the abnormal neurological activity, wherein the portion of the predetermined theoretical zone of activity comprises at least one node of the neurological network;

determine at least two contacts of the thermo-coupled multi-contact electrodes to deliver a controlled ablative current through to create a temporary lesion that is at or near the at least one node of the neurological network;

receive conduction data within the predetermined theoretical zone of activity recorded by the plurality of the contacts of the plurality of thermo-coupled-multi-contact electrodes during the delivery of the controlled ablative current; and determine whether the temporary lesion stops the abnormal neurological activity and treats the neurological condition; and a pulse generator configured to generate the controlled ablative current to be delivered using the at least two contacts of the plurality of thermo-coupled multi-contact electrodes to create the temporary lesion at the at least one node of the neurological network, wherein:

when the computing device determines the temporary lesion treats the neurological condition, based on the conduction data recorded during the delivery of the controlled ablative current to create the temporary lesion, then the pulse generator is configured to generate another controlled ablative current that creates a permanent lesion, and when the computing device determines the temporary lesion does not treat the neurological condition based on the conduction data recorded during the delivery of the controlled ablative current to create the temporary lesion, then the pulse generator is configured to send another controlled ablative current to another contact to create another temporary lesion at another at least one node of the neural network using the other contact.

6. The system of claim 5, wherein the plurality of contacts comprise at least four contacts.

7. The system of claim 5, wherein the plurality of contacts comprise at least ten contacts.

8. The system of claim 5, wherein at least two of the plurality of contacts are of different shapes.

9. The system of claim 5, wherein at least two of the plurality of contacts are of different sizes.

10. The system of claim 5, wherein the temperature sensor monitors a temperature rise while the temporary lesion is created so that the creation of the temporary lesion ends when the temperature rise rises to a predetermined threshold value indicating the temporary lesion is fully formed.

11. The system of claim 5, wherein the processor executes the instructions to determine the predetermined zone of activity based on an analysis of a frequency of the abnormal neurological activity and/or a centrality of the abnormal neurological activity.

12. The system of claim 5, wherein the processor executes the instructions to generate a conduction map based on conduction data recorded before the delivery of the controlled ablative current, wherein the conduction map is used to detect the abnormal neurological activity.

13. The system of claim 5, wherein the processor further analyzes a frequency of the abnormal neurological activity and/or a centrality of the abnormal neurological activity based on conduction data recorded before the delivery of the controlled ablative current.

* * * * *